United States Patent [19]
Aoyama et al.

[11] Patent Number: 6,146,647
[45] Date of Patent: Nov. 14, 2000

[54] MULTI-LAYER LIGHTWEIGHT TEXTURE COMPOSITION

[75] Inventors: Yukari Aoyama; Toshikatsu Hayashi; Koji Abe, all of Yokohama, Japan

[73] Assignee: Shiseido Company, Ltd., Tokyo, Japan

[21] Appl. No.: 09/104,537

[22] Filed: Jun. 26, 1998

[30] Foreign Application Priority Data

Jun. 30, 1997 [JP] Japan ................................. 9-189268
May 26, 1998 [JP] Japan ................................. 10-161445

[51] Int. Cl.$^7$ ................................................. A61K 7/50
[52] U.S. Cl. .................. 424/401; 424/70.31; 424/78.03; 424/680; 514/938
[58] Field of Search .................. 424/677, 401, 424/70.31, 78.03, 680; 514/938

[56] References Cited

U.S. PATENT DOCUMENTS 5,182,105  1/1993  Takata et al. ..................... 424/78.02
5,599,528  2/1997  Igaki ................................ 424/59

FOREIGN PATENT DOCUMENTS 41 00 490   3/1992   Germany .
4-290810   10/1919   Japan .
2 206 048  12/1988   United Kingdom .

OTHER PUBLICATIONS

European Patent Office, Patent Abstracts of Japan; JP 4290810, Pub. Oct. 15, 1992.

European Patent Office, Patent Abstracts of Japan; JP 63165305, Pub. Jul. 8, 1988.

*Primary Examiner*—Diana Dudash
*Assistant Examiner*—Alysia Berman
*Attorney, Agent, or Firm*—Foley & Lardner

[57] ABSTRACT

A multi-layer lightweight texture composition containing, (i) an oil component; (ii) water; (iii) a polyol; (iv) a nonionic surfactant selected from stearic acid polyoxyethylene (degree of polymerization n=3–10) cetyl ether, stearic acid polyoxyethylene (n=4–12) stearyl ether, stearic acid polyoxyethylene (n=3–15) lauryl ether, isostearic acid polyoxyethylene (n=2–10) lauryl ether, monostearic acid glycerol, lauroylglutamic acid polyoxyethylene (n=2–5) octyldodecyl ether diester, lauroylglutamic acid dipolyoxyethylene (n=2–5) stearyl ether, polyoxyethylene (n=3–50) oleyl ether, polyoxyethylene (n=2–12) diisostearate, and sorbitan monooleate; and (v) a water-soluble salt.

4 Claims, No Drawings

MULTI-LAYER LIGHTWEIGHT TEXTURE COMPOSITION

BACKGROUND OF THE INVENTION

1. Field of the Invention

The present invention relates to a multi-layer lightweight texture composition. More specifically, it relates to a highly safe multi-layer lightweight texture composition having the suppressed stickiness and sliminess in feeling and capable of forming a stable and tidy multi-layer separated condition having a clear interface.

2. Description of the Related Art

Known in the past as a multi-layer cosmetic composition are combinations of two types or more of oils which are not compatible with each other, or combinations of water, an alcohol and an oil uncompatible therewith, or combinations of an aqueous phase and an alcohol layer. However, these multi-layer cosmetic compositions are not in good admixture composition, although white turbid or dispersed conditions can be obtained by shaking before use.

Furthermore, recently, a three-layer cosmetic composition using, as a surfactant, monoaliphatic acid polyoxyethylene glyceryl (see JP-A-4-290810). This cosmetic composition exhibits a transparent appearance and good emulsification dispersibility, when shaking, and can be transparently separated after allowing to stand.

However, since the above three-layer cosmetic composition is composed of a three-layer structure of an oil layer, a surfactant layer and a wetting layer and since the water layer is small and the amount of the surfactant is large (5–70% by weight), the stickness in feeling is given when formulated as a cosmetic water or emulsion and possible skin problems may occur for certain people. Also, when formulated as bath essence, the admixing conditions are not good, and therefore, the oil droplets are formed and sliminess in feeling is provided. In addition, there are problems in the appearance that the separation conditions of the multi-layer are unstable and the interface conditions are not good.

SUMMARY OF THE INVENTION

Accordingly, the objects of the present invention are to eliminate the above-mentioned problems of the prior art and to provide a highly safe multi-layer lightweight texture or cosmetic composition using a decreased amount of a surfactant, capable of suppressing stickiness and sliminess in feeling, of forming a stable and tidy multi-layer separated condition having a clear interface.

In accordance with the present invention, there is provided a multi-layer lightweight texture composition comprising:

(i) an oil component; (ii) water; (iii) a polyol; (iv) at least one nonionic surfactant selected from the group consisting of stearic acid polyoxyethylene (degree of polymerization n=3–10) cetyl ether, stearic acid polyoxyethylene (n=4–12) stearyl ether, stearic acid polyoxyethylene (n=3–15) lauryl ether, isostearic acid polyoxyethylene (n=2–10) lauryl ether, monostearic acid glycerol, lauroylglutamic acid polyoxyethylene (n=2–5) octyldodecyl ether diester, lauroylglutamic acid dipolyoxyethylene (n=2–5) stearyl ether, polyoxyethylene (n=3–50) oleyl ether, polyoxyethylene (n=2–12) diisostearate, and sorbitan monooleate; and
(v) a water-soluble salt.

DESCRIPTION OF THE PREFERRED EMBODIMENTS

According to the present invention, when the specified nonionic surfactants and water-soluble salts are formulated, in combination, into a multi-layer lightweight texture composition, it is possible, when compared with the conventional composition, a relative large amount of water can be formulated and the amount of a surfactant to be formulated can be decreased. Thus, a structure of aqueous layer-polyol layer-oil layer having stable interfaces is formed and, as a result, the desired multi-layer lightweight texture composition having the suppressed stickiness and sliminess in feeling can be obtained.

Among the multi-layer lightweight texture compositions according to the present invention, a three-layer lightweight texture or cosmetic composition for a bath is especially suitable.

In the present invention, the term "lightweight texture or cosmetic composition" includes, in addition to cosmetics defined in the Drugs, Cosmetics and Medical Instruments Act, those usable in the make up belonging to, for example, quasi-drugs and drugs or pharmaceuticals, such as creams, lotions, rinses, treatments, hair cosmetics, perfumes, detergents, bath products.

The constructions or structures of the present invention will now be explained in detail.

The oil component formulated into the multi-layer lightweight texture composition according to the present invention is not specifically limited. Typical examples of the oil component are as follows.

Liquid oils such as avocado oil, tsubaki oil, turtle oil, macadamia nut oil, corn oil, mink oil, olive oil, rapeseed oil, yolk oil, sesame oil, parsic (phonetic) oil, wheat-germ oil, sasanqua oil, castor oil, linseed oil, safflower oil, cottonseed oil, perilla oil, soybean oil, peanut oil, teaseed oil, kaya oil, rice bran oil, china paulownia oil, Japanese paulownia oil, jojova oil, germ oil, triglycerol, trioctanic acid glycerol, tripalmutic acid glycerol, etc.;

Solid oils and fats such as cacao fat, coconut oil, horse fat, hydrogenated coconut oil, palm oil, beef tallow, mutton tallow, hydrogenated beef tallow, palm kernel oil, hog fat (or lard), beef bone fat, Japan tallow kernel oil, hydrogenated oil, beef leg fat, Japan tallow, hydrogenated castor oil, etc.;

Hydrocarbon oils such as liquid paraffin, ozocerite, squalene, pristane, paraffin, ceresine, vaseline, mycrocrystalline wax, etc.;

Synthetic ester oils such as isopropyl myristate, cetyl octanate, octyldodecyl myristate, isopropyl palmitate, butyl stearate, hexyl laurate, myristyl myristate, decyl oleate, hexyldecyl dimethyloctanate, cetyl lactate, myristyl lactate, lanolin acetate, isocetyl stearate, isocetyl isostearate, cholesteryl 12-hydroxystearate, di-2-ethylhexylic acid ethylene glycol, fatty acid ester of dipentaerythritol, monoisostearic acid N-alkylglycol, dicapric acid neopentylglycol, diisostearyl maleate, di-2-heptylundecanoic acid glycol, trimethylolpropane tri-2-ethylhexylinate, trimethylolpropane triisostearate, pentaerythritol tetra-2-ethyl-hexylinate, tri-2-ethylhexylic acid glycerol, cetyl-2-ethylhexanoate, 2-ethylhexylpalmitate, trimyristic acid glycerol, tri-2-heptylundecanoic acid glyceride, castor oil fatty acid methyl ester, oleinic acid oil, cetosteraryl alcohol, acetglyceride, palmitic acid-2-heptylundecyl, diisopropyl adipate, N-lauroyl-L-glutamic acid-2-octyldodecyl ester, adipic acid-2-heptyl undecyl, ethyllaurate, di-2-ethylhexyl sebacate, 2-hexyldecyl myristate, 2-hexydecyl palmitate, 2-hexyldecyl adipate, diisopropyl sebacate, 2-ethylhexyl succinate, ethyl acetate, butyl acetate, amyl acetate, triethyl citrate; and Silicones including linear polysiloxanes such as dimethylpolysiloxane, methylphenylpolysiloxane, methyl hydrogen polysiloxane, and cyclic polysiloxanes such as decamethyl polysiloxane, dodecamethyl polysiloxane, tetramethyl tetrahydrogen polysiloxane. Among these oil components, the use of liquid paraffin is preferable due to the formation of a stable layer.

The preferable amount of the oil component in the multi-layer lightweight texture composition according to the present invention is 10.0 to 78.0% by weight, more preferably 30.0 to 40.0% by weight, based upon the total amount of the composition.

The polyols formulated into the multi-layer lightweight texture composition according to the present invention are not specifically limited. Typical examples of the polyols usable in the present invention are dihydric alcohols such as ethylene glycol, propylene glycol, 1,3-butylene glycol, hexylene glycol; trihydric alcohols such as glycerol; tetrahydric alcohols such as pentaerythritol; pentahydric alcohols such as xylitol; hexahydric alcohols such as sorbitol, mannitol; polyhydric alcohol polymer such as diethylene glycol, dipropylene glycol, diglycerol, polyethylene glycol; dihydric alcohol alkyl ether such as ethylene glycol monomethyl ether, ethylene glycol dibutyl ether; trihydric alcohol alkyl ether such as diethylene glycol monomethyl ether. Among these polyhydric alcohols, the use of the hexylene glycol is preferable due to the formation of a stable layer.

The preferable amount of the polyol or polyhydric alcohol formulated in the multi-layer lightweight composition according to the present invention is 10.0 to 78.0% by weight, more preferably 30.0 to 40.0% by weight, based upon the total amount of the composition.

The nonionic surfactants formulated into the multi-layer lightweight texture composition according to the present invention include, for example, polyoxyethylene (degree of polymerization n=3) cetyl ether stearate (i.e., "POE(3) cetyl ether stearate" hereinbelow), POE(5) cetyl ether stearate, POE(7) cetyl ether stearate, POE(10) cetyl ether stearate, POE(4) stearyl ether stearate, POE(6) stearyl ether stearate, POE(9) stearyl ether stearate, POE(10) stearyl ether stearate, POE(12) stearyl ether stearate, POE(3) lauryl ether stearate, POE(5) lauryl ether stearate, POE(8) lauryl ether stearate, POE(10) lauryl ether stearate, POE(15) lauryl ether stearate, POE(2) lauryl ether isostearate, POE(5) lauryl ether isostearate, POE(8) lauryl ether isostearate, POE(10) lauryl ether isostearate, monostearic acid glycerol, lauroylglutamic acid POE(2) octyldodecyl ether diester, lauroyl glutamic acid POE(5) octyldodecyl ether diester, lauroyl glutamic acid di-POE(2) stearyl ether, lauroyl glutamic acid di-POE (5) stearyl ether, POE(5) oleyl ether, POE(12) diisostearate, sorbitan monooleate.

The preferable nonionic surfactants are polyoxyethylene (n=3–50) oleyl ether or polyoxyethylene (n=2–12) diisostearate. Among these nonionic surfactants, especially the use of POE(5) oleyl ether and POE(12) diisostearate is preferable.

The preferable amount of the nonionic surfactant to be formulated in the composition according to the present invention is 1.0 to 50.0% by weight, more preferably 1.0 to 5.0% by weight, based upon the total amount of the composition. When the amount of the nonionic surfactant is less than 1.0% by weight, or more than 50.0% by weight, based upon the total amount of the composition, the useability or applicability becomes poor.

The water-soluble salts formulated into the multi-layer lightweight texture composition according to the present invention are not specifically limited. The typical examples of the water-soluble salts are sodium chloride, potassium chloride, sodium sulfate, magnesium sulfate, sodium carbonate, calcium carbonate, sodium sulfite sodium citrate, sodium hydrogen phosphate, disodium hydrogen phosphate, trisodium hydrogen phosphate.

The water-soluble salt is formulated in the multi-layer lightweight texture composition according to the present invention in an amount sufficient to form the multi-layer structure of three layers or more. The amount is preferably 1.0 to 25.0% by weight, more preferably 10.0 to 15.0%, especially preferably 10.0 to 15.0% by weight, based upon the total composition. When the amount of the water-soluble salt formulated in the present composition is less than 1.0% by weight, the formation of a multi-layer structure of three layers or more becomes difficult. Contrary to this, when the amount is more than 25.0% by weight, the salt tends to be precipitated.

The amount of water to be formulated into the multi-layer lightweight texture composition according to the present invention is preferably 10.0 to 78.0% by weight, more preferably 30.0 to 40.0% by weight, based upon the total amount of the composition.

The type of formulation of the present multi-layer composition is not specifically limited and the present composition can be applied to all types of cosmetics in a broader sense. The application can be widely spread, for example, basic cosmetics such as lotion emulsion and special cosmetics for, for example, a bath use. Among these, the application to cosmetics for a bath use is particularly suitable.

The multi-layer lightweight texture composition according to the present invention can be formulated by, for example, previously preparing the aqueous phase, the oil phase and the polyhydric alcohol (or polyol) phase separately, followed by mixing the same, or by adding each component in any order.

EXAMPLES

The present invention will now be further illustrated in detail by, but is by no means limited to, the following Examples, wherein "percents" are all by weight unless otherwise noted.

Example 1

Three-Layer Type Cosmetic for BATH

| Component | % |
|---|---|
| Liquid paraffin | 35.0 |
| Antioxidant | q.s. |
| Preservative | q.s. |
| Fragrant | q.s. |
| Hexylene glycol | 35.0 |
| Polyoxyethylene (5 mol) oleyl ether | 3.0 |
| Sodium chloride (Official) | 3.0 |
| Purified Water | Amount to 100% in total |

(Preparation)

The oil phase, the polyol phase and the aqueous phase were separately prepared, followed by mixing them to obtain the desired three-layer type cosmetic for bath.

Example 2

Three-Layer Type Cosmetic for BATH

| Component | % |
| --- | --- |
| Liquid paraffin | 35.0 |
| Antioxidant | q.s. |
| Preservative | q.s. |
| Fragrant | q.s. |
| Hexylene glycol | 35.0 |
| Polyoxyethylene (12 mol) diisostearate | 3.0 |
| Sodium chloride (Official) | 3.0 |
| Purified water | Amount to 100% in total |

(Preparation)

The oil phase, the polyol phase and the aqueous phase were separately prepared, followed by mixing them to obtain the desired three-layer type cosmetic for bath.

Comparative Example 1

Three-Layer Type Cosmetic for BATH

| Component | % |
| --- | --- |
| Liquid paraffin | 30.0 |
| Fragrant | 2.7 |
| Antioxidant | q.s. |
| Preservative | q.s. |
| Glycerol | 34.7 |
| Coconut oil polyoxyethylene glycerol (7EO) | 29.7 |
| Purified water | 2.9 |
| Colorant (water-soluble) | q.s. |

(Preparation)

The oil phase, the polyol phase and the aqueous phase were separately prepared, followed by mixing them to obtain the desired three-layer type cosmetic for bath.

Comparative Example 2

Three-Layer Type Cosmetic for BATH

| Component | % |
| --- | --- |
| Liquid paraffin | 45.0 |
| Fragrant | 3.0 |
| Antioxidant | q.s. |
| Preservative | q.s. |
| Glycerol | 45.0 |
| Coconut oil polyoxyethylene glycerol (7EO) | 3.0 |
| Purified water | 3.0 |
| Colorant (water-soluble) | q.s. |

(Preparation)

The oil phase, the polyol phase and the aqueous phase were separately prepared, followed by mixing them to obtain the desired three-layer type cosmetic for bath.

Comparative Example 3

Three-Layer Type Cosmetic for BATH

| Component | % |
| --- | --- |
| Liquid paraffin | 35.0 |
| Antioxidant | q.s. |
| Preservative | q.s. |
| Fragrant | q.s. |
| Hexylene glycol | 35.0 |
| Polyoxyethylene (5 mol) oleyl ether | 3.0 |
| Purified water | Amount to 100% in total |

(Preparation)

The oil phase, the polyol phase and the aqueous phase were separately prepared, followed by mixing them to obtain the desired three-layer type cosmetic for bath.

Comparative Example 4

Three-Layer Type Cosmetic for BATH

| Component | % |
| --- | --- |
| Liquid paraffin | 35.0 |
| Antioxidant | q.s. |
| Preservative | q.s. |
| Fragrant | q.s. |
| Hexylene glycol | 35.0 |
| Coconut oil polyoxyethylene glycerol (7EO) | 3.0 |
| Sodium chloride (Official) | 3.0 |
| Purified water | Amount to 100% in total |

(Preparation)

The oil phase, the polyol phase and the aqueous phase were separately prepared, followed by mixing them to obtain the desired three-layer type cosmetic for bath.

The three-layer type cosmetics for bath of Examples and Comparative Examples prepared above were evaluated by the organoleptic feeling test when used and the stability test of the interface mentioned below. The results are shown in Table 1.

1. Organoleptic feeling test when used 20–25 ml of each sample was added, after shaking, to a 200 liters bathtub, followed by well agitating. Thereafter, a panel (male and female), at an age of 25 to 40. The results in the feeling test are evaluated according to the following criteria.

++: Less than 5 persons have the stickiness in feeling

+: 5 to less than 10 persons have the stickiness in feeling

±: 10 to less than 30 persons have the stickiness in feeling

−: 30 or more persons have the stickiness in feeling

2. Stability test of the interface

The formation of stable interface was visually evaluated according to the following criteria. The results are shown in Table 1.

| Evaluation | Time to acknowledgement of separation | Time to complete separation |
| --- | --- | --- |
| ++ | about 1 min | 1–2 min |
| + | 1–2 min | 30–60 min |
| ± | 1–2 min | more than 60 min |

|  | Example | | Comparative Example | | | |
| --- | --- | --- | --- | --- | --- | --- |
|  | 1 | 2 | 1 | 2 | 3 | 4 |
| Stickiness in Feeling | ++ | ++ | ± | ± | + | ± |
| Formation of Stable Interface | ++ | ++ | ± | ± | ± | + |

As is clear from the results shown in Table 1, the multi-layer type lightweight texture compositions of Examples 1 and 2 (i.e., three-layer type cosmetics for bath) according to the present invention are excellent in the stickiness in feeling and the formation of the stable interface.

Example 3
Three-Layer Type Cleansing Oil

| Component | % |
| --- | --- |
| Liquid paraffin | 20.0 |
| 2-Ethylhexyl palmitate | 5.0 |
| Silicone oil | 5.0 |
| Antioxidant | q.s. |
| Preservative | q.s. |
| Fragrant | q.s. |
| Hexylene glycol | 30.0 |
| Polyoxyethylene (5 mol) oleyl ether | 3.0 |
| Sodium chloride (Official) | 3.0 |
| Glycerol | q.s. |
| Peony root extract | q.s. |
| Ginseng extract | q.s. |
| Garenia Florida extract | q.s. |
| Mugwort extract | q.s. |
| Purified water | Amount to 100% in total |

(Preparation)

The oil phase, the polyol phase and the aqueous phase were separately prepared, followed by mixing them to obtain the desired three-layer type cleansing oil. The resultant three-layer type cleansing oil forms the aqueous layer-polyol layer-oil layer having stable interfaces and have no stickiness in feeling.

Example 4
Three-Layer Type Lotion

| Component | % |
| --- | --- |
| Squalane | 5.0 |
| Silicone oil | 5.0 |
| Antioxidant | q.s. |
| Preservative | q.s. |
| Fragrant | q.s. |
| Propylene glycol | 10.0 |
| Sorbitan monooleate | 3.0 |

| Component | % |
| --- | --- |
| Sodium chloride (Official) | 5.0 |
| Purified water | Amount to 100% in total |

(Preparation)

The oil phase, the polyol phase and the aqueous phase were separately prepared, followed by mixing them to obtain the desired three-layer type lotion. The resultant three-layer type lotion forms the aqueous layer-polyol layer-oil layer having stable interfaces and have no stickiness in feeling.

Example 5

The three-layer type cosmetic for bath having the same composition as in Example 1, except that the components were added in order instead of the separate preparation of the oil phase, the polyol phase and the aqueous phase. The resultant three-layer type cosmetic for bath forms the aqueous layer-polyol layer-oil layer having stable interfaces and have no stickiness in feeling.

As described above, the multi-layer type lightweight texture composition according to the present invention have no stickiness and sliminess in feeling and form the stable tidy multi-layer separation condition having a clear interface.

What is claimed is:

1. A multi-layer lightweight texture composition comprising:

(i) 10.0 to 78.0% by weight of liquid paraffin;

(ii) 10.0 to 78.0% by weight of water;

(iii) 10.0 to 78.0% by weight of hexylene glycol;

(iv) 1.0 to 50.0% by weight of at least one nonionic surfactant selected from the group consisting of stearic acid polyoxyethylene cetyl ether, wherein the polyoxyethylene has a degree of polymerization (n) of from 3 to 10; stearic acid polyoxyethylene stearyl ether, wherein the polyoxyethylene has an n of from 4 to 12; stearic acid polyoxyethylene lauryl ether, wherein the polyoxygethylene has an n of from 3 to 15; isostearic acid polyoxyethylene lauryl ether, wherein the polyoxyethylene has an n of from 2 to 10; monostearic acid glycerol, lauroylglutamic acid polyoxyethylene octyidodecyl ether diester, wherein the polyoxyethylene has an n of from 2 to 5, lauroylglutamic acid dipolyoxyethylene stearyl ether, wherein the polyoxyethylene has an n of from 2 to 5, polyoxyethylene oleyl ether, wherein the polyoxyethylene has an n of from 3 to 50; polyoxyethylene diisosterate wherein the polyoxyethylene has an n of from 2 to 12; and sorbitan monoleate; and (v) 1.0 to 25.0% by weight of a water-soluble salt.

2. A multi-layer lightweight texture composition as claimed in claim 1, wherein said nonionic surfactant is polyoxyethylene oleyl ether, wherein the polyoxyethylene has an n of from 3 to 50; or polyoxyethylene diisostearate wherein the polyoxyethylene has an n of from 2 to 12.

3. A three-layer lightweight texture composition for a bath as claimed in claim 1.

4. A three-layer composition for a bath as claimed in claim 2.

* * * * *